(12) United States Patent
Spakevicius et al.

(10) Patent No.: US 11,304,913 B2
(45) Date of Patent: *Apr. 19, 2022

(54) ANALGESIC COMPOSITIONS

(71) Applicant: Vapogenix, Inc., Houston, TX (US)

(72) Inventors: Danguole Spakevicius, Houston, TX (US); Heather Giles, Houston, TX (US); Terry Farmer, Houston, TX (US)

(73) Assignee: Vapogenix, Inc., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/869,797

(22) Filed: May 8, 2020

(65) Prior Publication Data

US 2021/0077423 A1  Mar. 18, 2021

Related U.S. Application Data

(60) Continuation of application No. 16/564,649, filed on Sep. 9, 2019, now Pat. No. 10,688,062, which is a
(Continued)

(51) Int. Cl.
*A61K 31/08* (2006.01)
*A61K 31/02* (2006.01)
(Continued)

(52) U.S. Cl.
CPC .......... *A61K 31/08* (2013.01); *A61K 9/0014* (2013.01); *A61K 9/06* (2013.01); *A61K 9/08* (2013.01);
(Continued)

(58) Field of Classification Search
CPC ...... A61K 31/08; A61K 9/0014; A61K 47/22; A61K 9/06; A61K 47/32; A61K 9/08;
(Continued)

(56) References Cited

U.S. PATENT DOCUMENTS 3,216,897 A   11/1965  Krantz
7,736,537 B1   6/2010  Zastrow et al.
(Continued)

FOREIGN PATENT DOCUMENTS

CN   101791291 A   8/2010
CN   102458557 A   5/2012
(Continued)

OTHER PUBLICATIONS

"Handbook of Chemical Products—Organic Chemical Materials (vol. 1)", Institute of Science and Technology Information, Ministry of Chemical Industry; Chemical Industry Press, 1985, pp. 151.
(Continued)

*Primary Examiner* — Taylor V Oh
(74) *Attorney, Agent, or Firm* — Saul Ewing Arnstein & Lehr LLP; Kathryn Doyle; Domingos J. Silva

(57) ABSTRACT

The present invention provides compositions useful in reducing or preventing pain in a subject in need thereof. In one embodiment, the compositions comprise a halogenated volatile compound. The present invention further includes a method of reducing or preventing pain in a subject in need thereof, the method comprising administering to the subject a therapeutically effective amount of a composition of the invention. Dosing regimens contemplated within the invention include one-time administration, continuous administration or periodic administration.

37 Claims, 4 Drawing Sheets

Related U.S. Application Data continuation of application No. 15/971,781, filed on May 4, 2018, now Pat. No. 10,507,189, which is a continuation of application No. 15/585,932, filed on May 3, 2017, now Pat. No. 10,071,065, which is a division of application No. 14/775,584, filed as application No. PCT/US2014/028169 on Mar. 14, 2014, now Pat. No. 9,655,867.

(60) Provisional application No. 61/814,485, filed on Apr. 22, 2013, provisional application No. 61/792,383, filed on Mar. 15, 2013.

(51) Int. Cl.

| | | |
|---|---|---|
| A61K 47/10 | (2017.01) | |
| A61K 47/20 | (2006.01) | |
| A61K 47/38 | (2006.01) | |
| A61K 9/00 | (2006.01) | |
| A61K 47/22 | (2006.01) | |
| A61K 9/06 | (2006.01) | |
| A61K 47/32 | (2006.01) | |
| A61K 9/08 | (2006.01) | |
| A61K 9/70 | (2006.01) | |
| A61K 47/12 | (2006.01) | |
| A61K 47/34 | (2017.01) | |

(52) U.S. Cl.
CPC .............. *A61K 9/70* (2013.01); *A61K 9/7023* (2013.01); *A61K 31/02* (2013.01); *A61K 47/10* (2013.01); *A61K 47/12* (2013.01); *A61K 47/20* (2013.01); *A61K 47/22* (2013.01); *A61K 47/32* (2013.01); *A61K 47/34* (2013.01); *A61K 47/38* (2013.01)

(58) Field of Classification Search
CPC ........ A61K 9/7023; A61K 9/70; A61K 47/12; A61K 47/34; A61K 47/10; A61K 47/20; A61K 47/38; A61K 31/02; A61P 29/02; A61P 25/04; A61P 23/02; A61P 17/02
USPC .......................................... 514/722
See application file for complete search history.

(56) References Cited

U.S. PATENT DOCUMENTS

| | | |
|---|---|---|
| 9,655,867 B2 | 5/2017 | Spakevicius et al. |
| 10,071,065 B2 | 9/2018 | Spakevicius et al. |
| 10,507,189 B2 | 12/2019 | Spakevicius et al. |
| 2005/0079147 A1 | 4/2005 | Delaey et al. |
| 2011/0159078 A1 | 6/2011 | Burton et al. |
| 2012/0071533 A1 | 3/2012 | Vontz et al. |
| 2012/0171281 A1 | 7/2012 | Spakevicius et al. |

FOREIGN PATENT DOCUMENTS

| | | |
|---|---|---|
| GB | 1547225 A | 6/1979 |
| JP | S62281814 A | 12/1987 |
| JP | 2003520769 U | 7/2003 |
| JP | 2006504740 A | 2/2006 |
| JP | 2006505611 A | 2/2006 |
| JP | 2007505047 A | 3/2007 |
| JP | 2011510091 A | 3/2011 |
| JP | 2011510092 A | 3/2011 |
| JP | 2012526133 A | 10/2012 |
| JP | 2014520157 A | 8/2014 |
| WO | 0072820 A2 | 12/2000 |
| WO | 2004032858 A2 | 4/2004 |
| WO | 2004043428 A2 | 5/2004 |
| WO | 2005023175 A4 | 3/2005 |
| WO | 2008036858 A2 | 3/2008 |
| WO | 2009094459 A1 | 7/2009 |
| WO | 2009094460 A2 | 7/2009 |
| WO | 2009117489 A1 | 9/2009 |
| WO | 2010129686 A1 | 11/2010 |
| WO | 2012177840 A1 | 12/2012 |
| WO | 2013004838 A1 | 1/2013 |
| WO | 2013016511 A1 | 1/2013 |

OTHER PUBLICATIONS

Ardente, et al., "Vehicle Effects on in vitro Transdermal Absorption of Sevoflurane in the Bullfrog, *Rana catesbeiana*", Environmental Toxicology and Pharmacology, vol. 25, No. 3., 2008, pp. 373-379.

Geronimo-Pardo, M., et al., "Analgesic Effect of Topical Sevoflurane on Venous Leg Ulcer with Intractable Pain", Phlebologie, vol. 2, 2011, pp. 95-97.

Inoue, S., et al., "Mild Hypothermia can Enhance Pial Arteriolar Vasodilation Induced by Isoflurane and Sevoflurane in Cats", Critical Care Medicine, vol. 30, No. 8, 2002, pp. 1863-1869.

Smith, J.M., et al., "Isoflurane Anesthesia in the African Clawed Frog (*Xenopus laevis*)", Contemporary Topics in Laboratory Animal Science, vol. 39, No. 6, 2000, pp. 39-42.

Smith, et al., "Isoflurane anesthesia in the African clawed frog", Contemporary Topics in Laboratory Animal Science, vol. 39, No. 6, Nov. 1, 200, pp. 39-42.

Wen, et al., "Effect of Anesthetic Molecules (Halothane and Isoflurane) on the Aggregation Behavior of POE-POP-POE Triblock Copolymers", J Phys Chem, Part B, vol. 103, No. 14, Mar. 20, 1999, pp. 2620-2626.

European Search Report dated Jun. 7, 2021 for European Patent Application EP 21 16 1625.5.

FIG. 1A

| PEG-3350 | Isopropyl Alcohol | Hydroxypropyl Cellulose MF | Hydroxypropyl Cellulose GF | 2-(2-ethoxyethxy)-ethanol | Propylene Carbonate | Gantrez ES-435 | PPG 400 | Alcohol 200 Proof | Propylene Glycol | PPG-12/SMDI copolymer | Oleic Acid | Dimethyl sulfoxide | Formulations |
|---|---|---|---|---|---|---|---|---|---|---|---|---|---|
|  |  |  |  |  |  |  |  |  |  |  |  |  | 101 |
|  |  |  |  |  |  |  |  |  |  |  |  | 50.00 | 201 |
|  |  |  | 2.00 |  |  |  |  |  |  |  | 10.00 | 28.00 | 202 |
|  |  |  | 5.00 |  |  |  |  |  |  |  |  | 25.00 | 203 |
|  |  |  | 1.75 |  |  |  |  |  | 14.75 |  | 3.00 |  | 204 |
| 6.00 |  |  |  | 10.00 |  |  |  | 10.00 | 5.00 |  |  |  | 205 |
|  |  |  | 2.00 |  |  |  | 15.00 |  |  |  |  | 23.00 | 206 |
|  |  |  |  |  |  |  |  |  |  |  |  |  | 207 |
|  | 20.00 | 2.00 |  |  |  |  |  |  | 8.00 |  |  |  | 208 |
|  |  |  | 1.75 |  |  |  |  |  |  |  |  | 38.25 | 209 |
|  |  |  | 1.75 |  |  |  |  | 14.25 | 15.00 |  | 3.00 |  | 210 |
|  |  |  |  | 5.00 | 2.50 | 20.00 |  | 12.50 |  |  |  |  | 211 |
|  | 2.00 |  |  | 5.00 | 2.50 | 20.00 |  | 10.50 |  |  |  |  | 212 |
|  |  |  |  | 5.00 |  |  |  |  |  |  |  | 35.00 | 213 |
|  |  |  | 1.75 |  |  |  |  | 10.00 | 15.25 |  | 3.00 |  | 214 |
|  |  |  |  | 10.00 |  |  |  |  | 15.00 |  |  |  | 215 |
|  |  |  | 1.75 |  |  |  | 20.00 | 8.25 |  | 10.00 |  |  | 216 |
|  |  |  |  |  |  |  |  |  |  |  |  | 40.00 | 217 |
|  |  |  |  | 5.00 |  |  |  |  |  |  |  | 10.00 | 218 |
|  |  |  |  | 5.00 |  |  |  |  |  |  |  | 20.00 | 219 |
|  |  |  | 2.25 |  |  |  |  |  | 14.75 |  | 3.00 |  | 220 |
|  |  |  | 2.00 |  |  |  |  |  | 15.00 |  | 3.00 |  | 221 |
|  |  |  | 1.75 |  |  |  | 20.00 |  |  |  |  |  | 222 |
|  |  |  | 2.00 |  |  |  | 20.00 |  |  |  |  | 18.00 | 223 |
|  |  |  |  | 5.00 |  |  |  |  |  |  |  | 5.00 | 224 |
|  |  |  | 1.75 |  |  |  |  | 10.00 | 15.25 | 10.00 | 3.00 |  | 225 |
|  |  | 2.50 |  |  |  |  |  |  |  |  |  | 37.50 | 226 |
|  |  |  | 1.75 |  |  |  |  | 15.00 | 20.25 |  | 3.00 |  | 227 |

| Formulations | Poloxamer 407 | Poloxamer 188 | Saccharine | PEG-300 | PEG-400 | Isoflurane (%) | Description | Rapid analgesia following topical application for 10 min. or less | Duration of analgesia (min.) |
|---|---|---|---|---|---|---|---|---|---|
| 101 | | | | | | 100.0 | Solution | ✓ | <20 |
| 201 | | | | | | 50.00 | Solution | ✓ | <30 |
| 202 | | | | | | 60.00 | Soft gel | | |
| 203 | | | | | | 70.00 | Gel | | |
| 204 | | | | | 20.50 | 60.00 | Soft gel | | |
| 205 | | | | | 9.00 | 60.00 | Ointment | ✓ | < 20 |
| 206 | | | | | | 60.00 | Soft gel | | |
| 207 | | | 2.00 | 78.00 | | 20.00 | Solution | | |
| 208 | | | | | | 70.00 | Ointment | | |
| 209 | | | | | | 60.00 | Soft gel | | |
| 210 | 1.00 | 5.00 | | | | 60.00 | Soft gel | | |
| 211 | | | | | | 60.00 | Clear solution | ✓ | > 60 |
| 212 | | | | | | 60.00 | Translucent gel | ✓ | >180 |
| 213 | | | | | | 60.00 | Gel | | |
| 214 | | | | | 10.00 | 60.00 | Soft gel | | |
| 215 | | | | | 15.00 | 60.00 | Solution | | |
| 216 | | | | | | 60.00 | Soft gel | ✓ | <200 |
| 217 | | | | | | 60.00 | Solution | | |
| 218 | | | | | | 85.00 | Gel | | |
| 219 | | | | | | 75.00 | Gel | | |
| 220 | | | | | 20.00 | 60.00 | Soft gel | ✓ | <60 |
| 221 | | | | | 20.00 | 60.00 | Soft gel | | |
| 222 | | | | | 18.25 | 60.00 | Soft gel | ✓ | >180 |
| 223 | | | | | | 60.00 | Soft gel | ✓ | < 40 |
| 224 | | | | | | 90.00 | Gel | | |
| 225 | | | | | | 60.00 | Soft gel | ✓ | <40 |
| 226 | | | | | | 60.00 | Soft gel | | |
| 227 | | | | | | 60.00 | Soft gel | | |

FIG. 1B

Mean responses to pinprick following 10 minute topical application of formulations (± SEM).
A) Formulation 212 (n = 8), B) Formulation 216 (n = 9).

ANALGESIC COMPOSITIONS

CROSS-REFERENCE TO RELATED APPLICATIONS

The present application is a continuation of, and claims priority to, U.S. patent application Ser. No. 16/564,649, filed Sep. 9, 2019, now U.S. Pat. No. 10,688,062, which is a continuation of, and claims priority to, U.S. patent application Ser. No. 15/971,781, filed May 4, 2018, now U.S. Pat. No. 10,507,189, which is a continuation of, and claims priority to U.S. patent application Ser. No. 15/585,932, filed May 3, 2017, now U.S. Pat. No. 10,071,065, which is a divisional of, and claims priority to, U.S. patent application Ser. No. 14/775,584, filed Sep. 11, 2015, now U.S. Pat. No. 9,655,867, which is a 35 U.S.C. § 371 national phase application from, and claims priority to, International Application No. PCT/US2014/028169, filed Mar. 14, 2014, which claims priority under 35 U.S.C. § 119(e) to U.S. Provisional Application No. 61/814,485, filed Apr. 22, 2013 and No. 61/792,383, filed Mar. 15, 2013, all of which applications are hereby incorporated by reference in their entireties herein.

BACKGROUND OF THE INVENTION

Pain is defined as an unpleasant sensory and emotional experience. Millions of people suffer from pain, ranging from minor headaches to debilitating chronic pain. Acute pain may be associated with a medical procedure or injury. Chronic pain may be associated with conditions such as cancer, HIV or diabetes. Currently available drugs used to treat pain have significant associated adverse effects, such as nausea, vomiting, tolerance, constipation, dyspepsia, myocardial infarction, stroke and chemical dependence.

An analgesic (also known as a painkiller) is the general name for a drug used to relieve pain (achieve analgesia). Analgesic drugs act through various mechanisms on the peripheral and central nervous systems. They include paracetamol (p-acetylamino phenol, also known as acetaminophen); the non-steroidal anti-inflammatory drugs (NSAIDs), such as the salicylates; opioid drugs, such as morphine and opium; and drugs for localized analgesia/anesthesia, such as lidocaine and benzocaine. Analgesics are distinct from general anesthetics, which reversibly render a patient unconscious and unaware of the surroundings. Local anesthesia leads to loss of feeling, whereas analgesia decreases the sensation of pain.

In choosing analgesics, the severity and response to medication determines the choice of compound. The WHO pain ladder, originally developed in cancer-related pain, is widely applied to find suitable compounds in a stepwise manner (Cancer pain relief and palliative care: Report of a WHO expert committee (1990). World Health Organization Technical Report Series, 804. Geneva, Switzerland: World Health Organization, pp. 1-75). The choice of analgesic is also determined by the type of pain: traditional analgesics are less effective for neuropathic pain, and classes of drugs not normally considered analgesics, such as tricyclic antidepressants and anticonvulsants (Dworkin et al., 2003, Arch. Neurol. 60 (11):1524-34), may be beneficial. For certain types of pain, such as pain associated with medical procedures or injury, localized analgesic effects may be important.

Venous access procedures, such as blood draws and IV starts, are a routine part of medical practice. These procedures are also the source of a considerable amount of pain and distress, particularly among children who require regular injections and/or venous access. Concern about the effect of such pain on children has been the focus of considerable study by the American Academy of Pediatrics (AAP), which devoted an entire supplement of Pediatrics on the issue (November 2008). As a result, the AAP and American Pain Society (APS) have adopted guidelines recommending the use of localized anesthetics to treat such pain whenever possible.

Pain associated with venous access procedures is not only the most common cause of pain in hospitalized children but also the second most common cause of "worst pain". Pediatric inpatients report IV line placement as the leading cause of procedure-related pain in the hospital, on par with post-surgical pain. Venipuncture causes not only moderate or severe pain in a significant number of pediatric inpatients, but also elevated levels of pre-procedural and procedural distress. Young children, even neonates, have highly refined pain-sensing systems. Continuous exposure to such pain can cause maladaptive pain response as an adult, but also the painful memory of such events can have significant psychological and physiological ramifications on later painful episodes.

Thus, considerable attention has been focused on the issue of preventing or reducing venous access pain in children. In fact, national and international organizations have proposed clinical guidelines recommending the use of local anesthetics in such cases, and such guidelines have been included in the hospital-accreditation process. Unfortunately, compliance with these guidelines is low. One of the major barriers to implementing the guidelines is the slow onset of action and resultant treatment delays associated with existing medications.

Currently, there is no pain medication that alleviates pain associated with minor procedures quickly, cost-effectively, and topically. Current pharmaceutical products are virtually all based on lidocaine, while other local anesthetics cannot easily penetrate intact human skin and cannot be used on large areas. Lidocaine-based creams take 45-60 minutes to begin taking effect, reaching maximum effect at about 120 minutes, and this slow onset limits their use in clinical settings.

Further, current topical analgesics' slow onset of action impedes their use for treating other procedural pain, such as that associated with painful cosmetic and medical dermatological procedures (for example mole removal, skin biopsies, Botox and fillers, aesthetic injections), with medical injections (such as immunizations, and insulin administration), with circumcision, heel sticks and other minor medical procedures as well as with non-medical uses (such as tattoos, tattoo removal and piercings).

An inhalational anesthetic possesses general anesthetic properties and can be delivered via inhalation. Inhalational anesthetics are administered by anesthetists through an anesthesia mask, laryngeal mask airway or tracheal tube connected to some type of anesthetic vaporizer and an anesthetic delivery system. Non-limiting examples of inhalational anesthetics include volatile anesthetics (such as isoflurane, sevoflurane, desflurane or aliflurane) and anesthetic gases (such as nitrous oxide or xenon).

Volatile anesthetics share the property of being liquid at room temperature, but evaporating easily for administration by inhalation. They are hydrophobic (i.e., as liquids, they are not freely miscible with water, and as gases they dissolve in oils better than in water). The ideal volatile anesthetic offers smooth and reliable induction and maintenance of general anesthesia with minimal effects on other organ systems. In addition, it is odorless or pleasant to inhale; safe for all ages and in pregnancy; not metabolized; rapid in onset and offset; potent; and safe for exposure to operating room staff. It is also cheap to manufacture; easy to transport and store, with a long shelf life; easy to administer and monitor with existing equipment; stable to light, plastics, metals, rubber and soda lime; non-flammable and environmentally safe. None of the volatile anesthetics currently in use are ideal, although many have some of the desirable characteristics. For example, sevoflurane is pleasant to inhale, rapid in onset/offset, and safe for all ages, but expensive and approximately half as potent as isoflurane. The full mechanism of action of volatile anesthetics is unknown and has been the subject of intense debate (Travis, 2004, Science News (July $3^{rd}$)).

There exists a need in the art for novel compositions that provide efficacious pain management for subjects in need thereof. These compositions should display good analgesic properties with minimal side effects or risks. These compositions should provide analgesia to a subject without compromising the subject's motor functions. These compositions should have manageable volatility, be chemically stable, and miscible and formulated with commercially acceptable excipients. For topical applications these compositions should penetrate human skin, preferably rapidly, and their effect should last for enough time to allow the performance of appropriate procedures. The present invention fulfills this need.

BRIEF SUMMARY OF THE INVENTION

In one aspect, the invention provides a composition comprising a halogenated volatile compound and at least one component selected from the group consisting of: an alcohol; 2-(2-ethoxyethoxy)-ethanol; a polyol; an organic solvent; an organic carbonate; hydroxypropyl cellulose (HPC); a fatty acid or a salt thereof; a polyethylene glycol (PEG); a polyethyne glycol (PPG); a monoester of a (methyl vinyl ether-maleic acid) co-polymer; a copolymer of 2-(2-hydroxypropoxy)propan-1-ol (PPG-12) and 1-methylene bis-4-isocyanatocyclohexane (SMDI); a poloxamer; saccharine, and any combinations thereof. In another aspect, the invention provides a method of reducing or preventing pain in a subject in need thereof, the method comprising administering to the subject a therapeutically effective amount of a composition of the invention, whereby pain in the subject is reduced or prevented. In yet another aspect, the invention provides a method of dressing a wound in a subject in need thereof, the method comprising applying to the wound a therapeutically effective amount of a composition of the invention.

In certain embodiments, the halogenated volatile compound is selected from the group consisting of isoflurane, halothane, enflurane, sevoflurane, desflurane, methoxyflurane, and any mixtures thereof. In other embodiments, the composition comprises about 5% to about 95% w/w halogenated volatile compound. In yet other embodiments, the composition comprises about 50% to about 90% w/w halogenated volatile compound.

In certain embodiments, the alcohol is selected from the group consisting of methanol, ethanol, n-propanol, isopropanol, n-butanol, sec-butanol, isobutanol, t-butanol, and any mixtures thereof. In other embodiments, the composition comprises about 2% to about 20% w/w alcohol. In yet other embodiments, the alcohol is ethanol and the composition comprises about 8.25%, about 10%, about 10.5%, about 12.5%, about 14.25%, about 15%, or about 20% w/w ethanol.

In certain embodiments, the composition comprises about 5% or about 10% w/w 2-(2-ethoxyethoxy)-ethanol.

In certain embodiments, the polyol is selected from the group consisting of ethylene glycol, propylene glycol, glycerol, and any mixtures thereof. In yet other embodiments, the composition comprises about 5% to about 20.25% w/w polyol. In yet other embodiments, the composition comprises about 5%, about 8%, about 14.75%, about 15%, about 15.25% or about 20.25% w/w polyol.

In certain embodiments, the organic solvent is selected from the group consisting of dimethylsulfoxide (DMSO), dimethylisosorbide, and any mixtures thereof. In other embodiments, the composition comprises from about 5% to about 50% w/w organic solvent. In yet other embodiments, the composition comprises from about 10% to about 50% w/w organic solvent.

In certain embodiments, the organic carbonate is selected from the group consisting of propylene carbonate, ethylene carbonate and any mixtures thereof. In other embodiments, the composition comprises about 2.5% w/w organic carbonate.

In certain embodiments, the HPC comprises HPC GF, HPC MF or any mixtures thereof. In other embodiments, the composition comprises from about 1% to about 5% w/w HPC. In yet other embodiments, the composition comprises about 1.75%, about 2%, about 2.25%, about 2.5%, or about 5% w/w HPC.

In certain embodiments, the fatty acid or salt thereof is selected from the group consisting of myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, and any combinations thereof. In other embodiments, the composition comprises from about 1% to about 5% w/w fatty acid or a salt thereof. In yet other embodiments, the composition comprises about 3% w/w fatty acid or a salt thereof.

In certain embodiments, the PEG is selected from the group consisting of PEG-200, PEG-300, PEG-400, PEG-600, PEG-[950-1,050], PEG-1,000, PEG-[1,300-1,600], PEG-[1,305-1,595], PEG-1,450, PEG-1,500, PEG-2,000, PEG-2,050, PEG-3,000, PEG-[3,000-3,700], PEG-3,350, PEG-4,000, PEG-4,600, PEG-6,000, PEG-8,000, PEG-10,000, PEG-12,000, PEG-20,000, PEG-35,000, and any mixtures thereof. In other embodiments, the composition comprises about 6% to about 78% w/w PEG. In yet other embodiments, the composition comprises about 6%, about 9%, about 10%, about 15%, about 18.25%, about 20%, about 20.5% or about 78% PEG.

In certain embodiments, the monoester of a (methyl vinyl ether-maleic acid) co-polymer is n-butyl, isopropyl, ethyl, or any mixtures thereof. In other embodiments, the composition comprises from about 15% to about 20% w/w monoester of a (methyl vinyl ether-maleic acid) co-polymer. In yet other embodiments, the composition comprises about 20% w/w monoester of a (methyl vinyl ether-maleic acid) co-polymer.

In certain embodiments, the composition comprises from about 5% to about 15% w/w copolymer of PPG-12 and SMDI. In other embodiments, the composition comprises about 10% w/w copolymer of PPG-12 and SMDI.

In certain embodiments, the composition comprises about 2% w/w saccharine.

In certain embodiments, the composition comprises about 15% to about 20% w/w PPG.

In certain embodiments, the composition comprises from about 1% to about 5% w/w poloxamer. In other embodiments, the poloxamer comprises poloxamer 188, poloxamer 407, and any mixtures thereof.

In certain embodiments, the composition is selected from the group consisting of: (a) about 50% w/w DMSO, and about 50% w/w isoflurane (201, FIGS. 1A-1B); (b) about 28% w/w DMSO, about 10% w/w copolymer of PPG-12 and SMDI, about 2% w/w HPC GF, and about 60% w/w isoflurane (202, FIGS. 1A-1B); (c) about 25% w/w DMSO, about 5% w/w HPC GF, and about 70% w/w isoflurane (203, FIGS. 1A-1B); (d) about 3% w/w oleic acid, about 14.75% w/w propylene glycol, about 1.75% w/w HPC GF, about 20.5% w/w PEG-400, and about 60% w/w isoflurane (204, FIGS. 1A-1B); (e) about 5% w/w propylene glycol, about 10% w/w ethanol, about 10% w/w 2-(2-ethoxyethoxy)ethanol, about 6% w/w PEG-3350, about 9% w/w PEG-400 and about 60% w/w isoflurane (205, FIGS. 1A-1B); (f) about 23% w/w DMSO, about 15% w/w PPG-400, about 2% w/w HPC GF, and about 60% w/w isoflurane (206, FIGS. 1A-1B); (g) about 2% w/w saccharine, about 78% w/w PEG-300, and about 20% w/w isoflurane (207, FIGS. 1A-1B); (h) about 8% w/w propylene glycol, about 2% w/w HPC MF, about 2% w/w isopropyl alcohol, and about 70% w/w isoflurane (208, FIGS. 1A-1B); (i) about 38.25% w/w DMSO, about 1.75% w/w HPC GF, and about 60% w/w isoflurane (209, FIGS. 1A-1B); (j) about 3% w/w oleic acid, about 15% w/w propylene glycol, about 14.25% w/w ethanol, about 1.75% w/w HPC GF, about 1% w/w poloxamer 407, about 5% w/w poloxamer 188, and about 60% w/w isoflurane (210, FIGS. 1A-1B); (k) about 12.5% w/w ethanol, about 20% w/w Gantrez ES-435, about 2.5% w/w propylene carbonate, about 5% w/w 2-(2-ethoxyethoxy)ethanol, and about 60% w/w isoflurane (211, FIGS. 1A-1B); (l) about 10.5% w/w ethanol, about 20% w/w Gantrez ES-435, about 2.5% w/w propylene carbonate, about 5% w/w 2-(2-ethoxyethoxy)ethanol, about 2% w/w HPC MF, and about 60% w/w isoflurane (212, FIGS. 1A-1B); (m) about 35% w/w DMSO, about 5% w/w HPC GF, and about 60% w/w isoflurane (213, FIGS. 1A-1B); (n) about 3% w/w oleic acid, about 15.25% w/w propylene glycol, about 10% w/w ethanol, about 1.75% w/w HPC GF, about 10% w/w PEG-400, and about 60% w/w isoflurane (214, FIGS. 1A-1B); (o) about 15% w/w propylene carbonate, about 10% w/w 2-(2-ethoxyethoxy) ethanol, about 15% w/w PEG-400, and about 60% w/w isoflurane (215, FIGS. 1A-1B); (p) about 10% w/w copolymer of PPG-12 and SMDI, about 8.25% w/w ethanol, about 20% w/w Gantrez ES-435, about 1.75% w/w HPC GF, and about 60% w/w isoflurane (216, FIGS. 1A-1B); (q) about 40% w/w DMSO, and about 60% w/w isoflurane (217, FIGS. 1A-1B); (r) about 10% w/w DMSO, about 5% w/w HPC GF, and about 85% w/w isoflurane (218, FIGS. 1A-1B); (s) about 20% w/w DMSO, about 5% w/w HPC GF, and about 75% w/w isoflurane (219, FIGS. 1A-1B); (t) about 3% w/w oleic acid, about 14.75% w/w propylene glycol, about 2.25% w/w HPC MF, about 20% w/w PEG-400, and about 60% w/w isoflurane (220, FIGS. 1A-1B); (u) about 3% w/w oleic acid, about 15% w/w propylene glycol, about 2% w/w HPC GF, about 20% w/w PEG-400, and about 60% w/w isoflurane (221, FIGS. 1A-1B); (v) about 20% w/w Gantrez ES-435, about 1.75% w/w HPC GF, about 18.25% w/w PEG-400, and about 60% w/w isoflurane (222, FIGS. 1A-1B); (x) about 18% w/w DMSO, about 20% w/w Gantrez ES-435, about 2% w/w HPC GF, and about 60% w/w isoflurane (223, FIGS. 1A-1B); (z) about 5% w/w DMSO, about 5% w/w HPC GF, and about 90% w/w isoflurane (224, FIGS. 1A-1B); (y) about 3% w/w oleic acid, about 10% w/w copolymer of PPG-12 and SMDI, about 15.25% w/w propylene glycol, about 10% w/w ethanol, about 1.75% w/w HPC GF, and about 60% w/w isoflurane (225, FIGS. 1A-1B); (w) about 37.5% w/w DMSO, about 2.5% w/w HPC MF, and about 60% w/w isoflurane (226, FIGS. 1A-1B); and (aa) about 3% w/w oleic acid, about 20.25% w/w propylene glycol, about 15% w/w ethanol, about 1.75% w/w HPC GF, and about 60% w/w isoflurane (227, FIGS. 1A-1B).

In certain embodiments, the composition is incorporated in a medical patch. In other embodiments, the wound is in the skin of the subject. In yet other embodiments, the composition is administered locally or regionally. In yet other embodiments, the composition is administered by at least one route from the group selected from intrathecally, epidurally, transdermally, topically, mucosally, buccally, rectally, vaginally, intramuscularly, subcutaneously, by local skin infiltration, and in a nerve block procedure. In yet other embodiments, the pain comprises chronic pain. In yet other embodiments, the composition comprises acute pain.

In certain embodiments, the administration of the composition is continuous. In other embodiments, the continuous delivery is achieved by a transdermal route or an infusion pump. In yet other embodiments, the administration of the composition is periodic. In yet other embodiments, the administration of the composition is a one-time event. In yet other embodiments, the administration of the composition is both periodically administered and continuously administered to the subject on separate occasions. In yet other embodiments, the pain reduction or prevention is achieved with little or no inhibition of motor function of the subject. In yet other embodiments, the subject is a mammal. In yet other embodiments, the subject is human, mouse or rat.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A-1B comprise a table illustrating compositions of the invention useful for topical application. The table comprises ingredients (% w/w), physical aspect descriptions, and results of in vivo testing using a rat pinprick model.

FIG. 2A: Formulation 212 (n=8), FIG. 2B: Formulation 216 (n=9).

DETAILED DESCRIPTION OF THE INVENTION

Figure 2A:
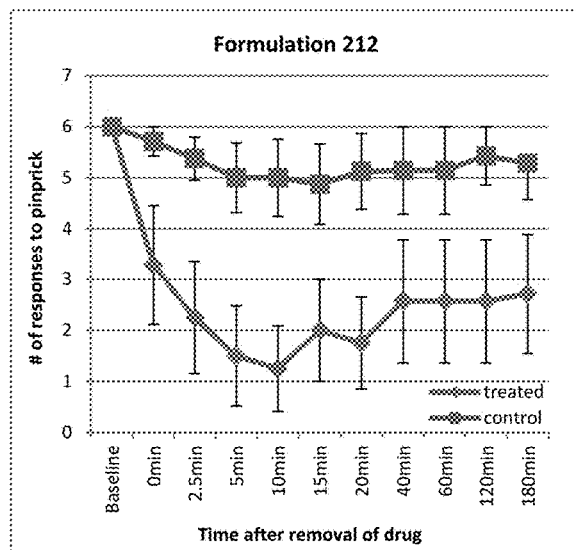
FIGS. 2A-2B are a series of graphs illustrating mean responses to pinprick following 10 minute topical application of selected formulations of the invention (±SEM).
Figure 2B:
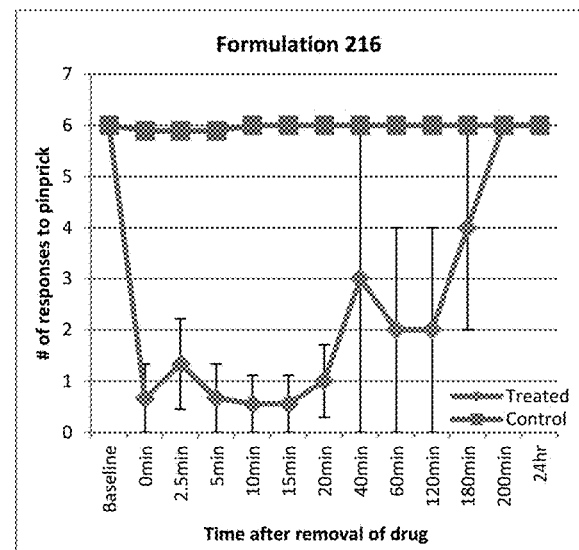

The present invention relates to the unexpected discovery that the compositions of the invention are effective in rapidly reducing or preventing pain in a subject in need thereof. In one embodiment, the compositions of the invention are delivering to the subject by a route other than orally, intravenously, or by inhalation.

The present invention further relates to the unexpected discovery that the compositions of the invention penetrate skin quickly, unlike the current topical pain medications, such as topical lidocaine (FIGS. 1A-1B). In contrast, unformulated volatile anesthetics quickly penetrate human skin, but are also quickly lost to the environment.

In one aspect, the compositions of the invention can be formulated so that the volatility of the volatile anesthetic is reduced (i.e., the volatile anesthetic evaporates at a reduced rate, and the composition of the invention retains its analgesic properties for extended periods of time) while maintaining its ability of penetrating skin quickly. In another aspect, the compositions of the invention have good miscibility with pharmaceutically acceptable carriers. In yet another aspect, the compositions of the invention are more viscous than unformulated volatile anesthetics and are thus easier to apply to the skin and do not disperse from the skin as quickly as unformulated volatile anesthetics.

The present invention overcomes limitations in the prior art by providing improved anesthetic compositions that are useful in reducing pain in a subject in need of such pain reduction, such as an animal patient or laboratory animal. In one embodiment, the animal is a mammal. In another embodiment, the mammal is human. In yet another embodiment, the compositions of the invention reduce or prevent pain in a subject without causing a loss of consciousness of the subject. In yet another embodiment, the compositions of the invention reduce or prevent pain in a subject without substantially interfering with the motor function of the subject.

In one aspect, the compositions of the invention are easily dispensed to a subject, and administration of a composition to the present invention to the subject can result in a very quick onset of analgesia in the subject. In another aspect, the compositions of the invention may quickly dissipate after administration, whereby analgesia may be rapidly ended. In yet another aspect, the compositions of the invention do not comprise opioid compounds, and this characteristics is advantageous from a practitioner's standpoint, because opioids possess certain disadvantages, including tolerance, drug interactions, and dependence.

In another aspect, the compositions of the invention are useful for dressing a wound in a subject. In one embodiment, the compositions of the invention reduce or prevent pain associated with the wound without causing a loss of consciousness of the subject. In another embodiment, the compositions of the invention reduce or prevent pain associated with the wound without substantially interfering with the motor function of the subject. In yet another embodiment, the compositions of the invention reduce the time of wound healing or recovery. In yet another embodiment, the wound is in the skin of the subject.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in organic chemistry, formulation chemistry and biology are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "topical" as applied to mode of administration includes but is not limited to "dermal." The term "dermal" refers to the application of a composition to the skin of a subject. The term "topical refers to the application of a composition to the body's natural surface, which has not been created by surgical intervention or any artificial means.

As used herein, the term "wound dressing" refers to an adjunct (such as a chemical and/or material) used by a person for application to a wound to promote healing and/or prevent further harm.

As used herein, the term "to dress a wound" refers to the act of applying an adjunct to the wound, in order to improve healing and/or prevent further harm.

As used herein, the terms "inhibiting," "reducing," and variations of these terms, include any measurable decrease, such as but not limited to complete or substantially complete inhibition.

As used herein, the term "preventing" as relating to a condition in a subject refers to the ability of avoiding the onset of the condition in a patient that is likely, susceptible or expected to develop the condition.

As used herein, the term "effective" means adequate to accomplish a desired, expected, or intended result.

As used herein, the term "or" means "and/or," unless explicitly indicated to refer to alternatives only or the alternatives are mutually exclusive, although the disclosure supports a definition that refers to only alternatives and "and/or."

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the terms "patient" and "subject" refer to a human or a non-human animals. Non-human mammals include, for example, livestock and pets, such as ovine, bovine, porcine, canine, feline and murine mammals. Preferably, the subject is human.

As used herein, the terms "effective amount," "pharmaceutically effective amount" and "therapeutically effective amount" refer to a nontoxic but sufficient amount of an agent to provide the desired biological result. That result can be reduction and/or alleviation of the frequency and/or severity of signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 20$^{th}$ Ed., 2000, Easton, Pa.), which is incorporated herein by reference.

As used herein, the language "pharmaceutically acceptable salt" refers to a salt of the administered compounds prepared from pharmaceutically acceptable non-toxic acids including inorganic acids, organic acids, solvates, hydrates, or clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, 3-hydroxybutyric, salicylic, galactaric and galacturonic acid. Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the "instructional material" includes a publication, a recording, a diagram, or any other medium of expression that may be used to communicate the usefulness of the compounds of the invention. In some instances, the instructional material may be part of a kit useful for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the compounds of the invention or be shipped together with a container that contains the compounds. Alternatively, the instructional material may be shipped separately from the container with the intention that the recipient uses the instructional material and the compound cooperatively. For example, the instructional material is for use of a kit; instructions for use of the compound; or instructions for use of a formulation of the compound.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

Compositions of the Invention

The compositions of the invention are described in a non-limiting manner herein. The compositions of the invention may be in a liquid, solid or viscous form. In one embodiment, the compositions of the inventions may be an ointment, a clear solution, a translucent gel, a soft gel, or any combination thereof. In another embodiment, the compositions of the invention comprise an emulsion. In yet another embodiment, the compositions of the invention comprise a liposome or microdroplet.

In one aspect, the compositions of the invention are free of water. In another aspect, the compositions of the invention comprise water. In one embodiment, the compositions of the invention comprise less than 5% water. In another embodiment, the compositions of the invention comprise less than 2.5% water. In yet another embodiment, the compositions of the invention comprise less than 1% water. In yet another embodiment, the compositions of the invention comprise less than 0.5% water. In yet another embodiment, the compositions of the invention comprise less than 0.1% water. In yet another embodiment, the compositions of the invention comprise less than 0.05% water. In yet another embodiment, the compositions of the invention are essentially free of water.

In one aspect, the compositions of the invention comprise a halogenated volatile compound selected from the group consisting of isoflurane, halothane, enflurane, sevoflurane, desflurane, methoxyflurane, and mixtures thereof. In one embodiment, the halogenated volatile compound is isoflurane. The compositions of the invention may comprise from about 5% to about 95% w/w, about 10% to about 90% w/w, about 20% to about 90% w/w, about 50% to about 90% w/w, about 60% to about 80% w/w, or about 60% to about 75% w/w halogenated volatile compound. In one embodiment, the compositions of the invention comprise about 20%, about 50%, about 60%, about 70%, about 75%, about 85% or about 90% halogenated volatile compound. Many of these compounds are racemic mixtures. In one embodiment, the racemic mixtures are used. In other embodiment, only the d-isomer or the l-isomer of the compound is used (for examples, see U.S. Pat. Nos. 5,114,715; 5,114,714; and 5,283,372)

In one aspect, the compositions of the invention comprise an alcohol. Non-limiting examples of alcohols contemplated within the invention include methanol, ethanol, n-propanol, isopropanol, n-butanol, sec-butanol, isobutanol, t-butanol, or any mixtures thereof. The compositions of the invention may comprise from about 1% to about 25% w/w, about 2% to about 20% w/w, about 5% to about 15% w/w, about 5% to about 10% w/w alcohol. In one embodiment, the compositions of the invention comprise about 8.25% w/w, about 10% w/w, about 10.5% w/w, about 12.5% w/w, about 14.25% w/w, about 15% w/w, or about 20% w/w alcohol.

In one aspect, the compositions of the invention comprise 2-(2-ethoxyethoxy)-ethanol. The compositions of the invention may comprise from about 1% to about 25% w/w, about 2% to about 20% w/w, about 5% to about 15% w/w, about 5% to about 10% w/w 2-(2-ethoxyethoxy)ethanol. In one embodiment, the compositions of the invention comprise from about 2% to about 10% w/w 2-(2-ethoxyethoxy)-ethanol. In another embodiment, the compositions of the invention comprise about 2.5% w/w, about 5% w/w, or about 10% w/w 2-(2-ethoxy ethoxy) ethanol.

In one aspect, the compositions of the invention comprise a polyol. Non-limiting examples of polyols contemplated within the invention include, but are not limited to, ethylene glycol, propylene glycol, glycerol or any mixtures thereof. The compositions of the invention may comprise from about 5% to about 20.25% w/w polyol. In one embodiment, the compositions of the invention comprise about 5% w/w, about 8% w/w, about 14.75% w/w, about 15% w/w, about 15.25% w/w, or about 20.25% w/w polyol.

In one aspect, the compositions of the invention comprise an organic solvent. Non-limiting examples of organic solvents contemplated within the invention are dimethylsulfoxide (DMSO), dimethylisosorbide, or any mixtures thereof. The compositions of the invention may comprise from about 5% to about 50% w/w organic solvent. In one embodiment, the compositions of the invention comprise about 5% w/w, about 10% w/w, about 18% w/w, about 20% w/w, about 23% w/w, about 25% w/w, about 28% w/w, about 35% w/w, about 37.5% w/w, about 38.25% w/w, about 40% w/w, or about 50% w/w DMSO.

In one aspect, the compositions of the invention comprise an organic carbonate. Non-limiting examples of organic carbonates contemplated within the invention are propylene carbonate and ethylene carbonate. The compositions of the invention may comprise from about 2.5% to about 20% w/w organic carbonate. In one embodiment, the compositions of the invention comprise about 2.5% w/w or about 20% w/w organic carbonate.

In one aspect, the compositions of the invention comprise hydroxypropyl cellulose (HPC). HPC (or 2-hydroxypropyl ether of cellulose) is a non-ionic water-soluble ether of cellulose in which some of the hydroxyl groups in the repeating glucose units have been hydroxypropylated forming —$OCH_2CH(OH)CH_3$ groups using propylene oxide. The average number of substituted hydroxyl groups per glucose unit is referred to as the degree of substitution (DS), with complete substitution providing a DS of 3. Because the hydroxypropyl group added contains a hydroxyl group, this can also be etherified during preparation of HPC. When this occurs, the number of moles of hydroxypropyl groups per glucose ring, moles of substitution (MS), can be higher than 3. Non-limiting examples of commercially available HPC are HPC GF, HPC MF, or any mixtures thereof. HPC GF has a solution viscosity of 150-400 mPas in water (2% per weight), and 75-400 mPas in ethanol (2% per weight). HPC MF has a solution viscosity of 4,000-6,500 mPas in water (2% per weight), and 3,000-6,500 mPas in ethanol (2% per weight). The compositions of the invention may comprise from about 1% to about 5% w/w HPC. In one embodiment, the compositions of the invention comprise about 1.75% w/w, about 2% w/w, about 2.25% w/w, about 2.5% w/w, or about 5% w/w HPC.

In one aspect, the compositions of the invention comprise a fatty acid or a salt thereof. Non-limiting examples of fatty acids contemplated within the invention are myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, or any mixtures thereof. The compositions of the invention may comprise from about 1% to about 5% w/w fatty acid or a salt thereof. In one embodiment, the compositions of the invention comprise about 3% w/w fatty acid or a salt thereof.

In one aspect, the compositions of the invention may comprise a polyethylene glycol (PEG). Non-limiting examples of PEGs contemplated within the invention are PEG-200, PEG-300, PEG-400, PEG-600, PEG-[950-1,050], PEG-1,000, PEG-[1,300-1,600], PEG-[1,305-1,595], PEG-1,450, PEG-1,500, PEG-2,000, PEG-2,050, PEG-3,000, PEG-[3,000-3,700], PEG-3,350, PEG-4,000, PEG-4,600, PEG-6,000, PEG-8,000, PEG-10,000, PEG-12,000, PEG-20,000, PEG-35,000, or any mixtures thereof, wherein the number associated with the PEG indicates the approximate average molecular weight of the oligomer or polymer. The compositions of the invention may comprise from about 5% to about 80% w/w PEG, or from about 6% to about 78% w/w PEG. In one embodiment, the compositions of the invention comprise about 6% w/w, about 9% w/w, about 10% w/w, about 15% w/w, about 18.25% w/w, about 20% w/w, about 20.5% or about 78% w/w PEG.

In one aspect, the compositions of the invention may comprise a polypropylene glycol (PPG). Non-limiting examples of PEGs contemplated within the invention are PPG-400, PPG-1000, PPG-1650, PPG-2250, and PPG-4000, or any mixtures thereof, wherein the number associated with the PPG indicates the approximate average molecular weight of the oligomer or polymer. The compositions of the invention may comprise from about 15% to about 20% w/w PPG, or about 15% w/w PPG.

In one aspect, the compositions of the invention may comprise a monoalkyl ester of a (methyl vinyl ether-maleic acid) co-polymer. In one embodiment, the ester is n-butyl (such as GANTREZ A-425®, GANTREZ ES-425®, or GANTREZ ES-435®), isopropyl (such as GANTREZ ES-335®), or ethyl (such as GANTREZ SP-215® or GANTREZ ES-225®). The compositions of the invention may comprise from about 15% to about 25% w/w monoester of a (methyl vinyl ether-maleic acid) co-polymer. In one embodiment, the compositions of the invention comprise about 20% w/w monoester of a (methyl vinyl ether-maleic acid) co-polymer.

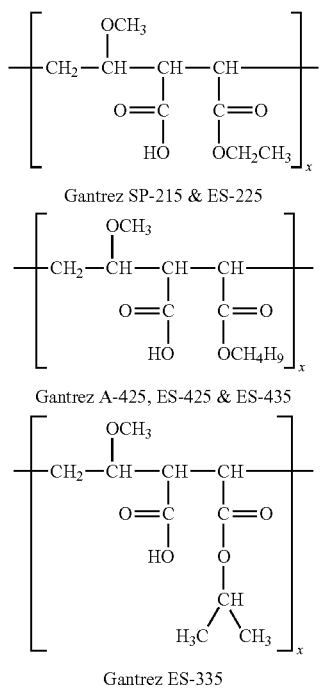

Gantrez SP-215 & ES-225

Gantrez A-425, ES-425 & ES-435

Gantrez ES-335

In one aspect, the compositions of the invention may comprise a copolymer of PPG-12 (also known as 2-(2-hydroxypropoxy)propan-1-ol) and SMDI (also known as 1,1-methylenebis4-isocyanatocyclohexane or methylene bis (4-cyclohexylisocyanate) polymer. In one embodiment, the compositions of the invention comprise about 5% w/w to about 15% w/w copolymer of PPG-12 and SMDI. In another embodiment, the compositions of the invention comprise about 10% w/w copolymer of PPG-12 and SMDI.

In one aspect, the compositions of the invention may comprise a poloxamer. Poloxamers are nonionic triblock copolymers composed of a central hydrophobic chain of polyoxypropylene (poly(propylene oxide)) flanked by two hydrophilic chains of polyoxyethylene (poly(ethylene oxide)). Poloxamers are also known by the trade names Synperonics, Pluronics and Kolliphor. For the generic term "poloxamer", these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=poloxamer with a polyoxypropylene molecular mass of 4,000 g/mol and a 70% polyoxyethylene content; P188=poloxamer with a polyoxypropylene molecular mass of 1,800 g/mol and a 80% polyoxyethylene content). For the Pluronic trade name, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit×10 gives the percentage polyoxyethylene content (e.g., L61=Pluronic with a polyoxypropylene molecular mass of 1,800 g/mol and a 10% polyoxyethylene content). In the example given, poloxamer 181 (P181)=Pluronic L61, poloxamer 407=Pluronic F127. In one embodiment, the compositions of the invention comprise from about 1% to about 5% w/w poloxamer, or about 1% w/w poloxamer, or about 5% w/w poloxamer. In another embodiment, the poloxamer comprises poloxamer 188 or poloxamer 407.

In one aspect, the compositions of the invention comprise saccharine. In one embodiment, the compositions of the invention comprise about 2% w/w saccharine.

Various concentrations of each component contemplated within the invention may be used to generate the composition of the invention. For example, a composition of the invention comprising a component may comprise about 0.1%-99%, 0.1%-60%, 5%-50%, 10%-40%, 5%-25%, 10%-30%, 10%-25%, 25%-50%, 10%-75%, 25%-75%, 10%-65%, 25%-65%, 10%-60%, 25%-60%, 0.1%, 1%, 5%, 10%, 20%, 25%, 30%, 35%, 40%, 45%, 50%, 55%, 60%, 65%, 70%, 75%, 80% or any range derivable therein, of the component.

In one aspect, the compositions of the invention further include at least one local anesthetic, such as but not limited to lidocaine, tetracaine, benzocaine, and prilocaine. In one embodiment, the at least one anesthetic is physically separated from the halogenated volatile compound. In another embodiment, the at least one anesthetic is in physical contact with the halogenated volatile compound.

The components of the compositions of the invention may be combined using methods known to those skilled in the art. Non-limiting procedures for preparing the compositions of the invention are provided in the Examples section.

The delivery of the volatile anesthetic composition may be continuous, periodic, a one-time event, or the volatile anesthetic composition may be both periodically administered and continuously administered to the subject on separate occasions.

At least one component of the compositions of the invention may provide substantial advantages, including improving the physical characteristics, pharmacological properties, and/or the ease of use of the halogenated volatile compound, wherein the at least one component is selected from the group consisting of an alcohol, an organic solvent, an organic carbonate, hydroxypropyl cellulose (HPC), a fatty acid or a salt thereof, a polyethylene glycol (PEG), a monoester of a (methyl vinyl ether-maleic acid) co-polymer, and any mixtures thereof. The at least one component may interact with the halogenated volatile compound in a non-azeotropic fashion to effectively reduce vaporization or evaporation of the halogenated volatile compound. In this way, the shelf-life, durability, skin penetrability, and/or ease of use of the halogenated volatile compound composition are improved. The at least one component may also improve the ease of mixing the composition prior to administration. Additionally, the pharmacokinetics of the halogenated volatile compound may be altered by the presence of the at least one component to provide improved pain relief. For example, without wishing to be bound by any theory, the at least one component may maintain the halogenated volatile compound in a particular region more effectively and/or help deliver the halogenated volatile compound to the site(s) of action.

The component may also increase the viscosity of the halogenated volatile compound. Increased viscosity of the halogenated volatile compound may also improve the ease of handling and applying the compositions of the invention.

The invention further contemplates using the compositions of the invention in medical patches. In one embodiment, the composition of the invention is incorporated in a medical patch, which is made of materials that are compatible with the composition of the invention. Preparation and use of a medical patch is known to those skilled in the art. The patch comprising the composition of the invention may be applied to the skin of the subject, providing localized analgesic relief thereof. In one embodiment, a composition of the invention may comprise from about 10% to about 100% w/w, about 20% to about 95% w/w, about 50% to about 90% w/w, about 60% to about 80% w/w, or about 60% to about 75% w/w halogenated volatile compound. In one embodiment, a composition of the invention comprises about 20%, about 50%, about 60%, about 70%, about 75%, about 85% or about 100% halogenated volatile compound.

The present invention also contemplates a sealed container comprising the composition of the present invention. The interior of the container may be sterile. The container may comprise a stopper which can be easily pierced by an injection needle. The container may comprise the chamber portion of a syringe. The container may comprise a drip chamber. The drip chamber may be coupled to a catheter. The catheter may be an epidural catheter or an intrathecal catheter. The container can be a syringe, a tube, a plastic bag, a collapsible plastic bag, a glass bottle, a glass ampoule, or a plastic bottle. The container may be coupled to an infusion pump. The infusion pump may be an intrathecal pump, an epidural delivery infusion pump, or a patient control analgesia (PCA) pump. The infusion pump may be programmable.

The halogenated volatile compound may be dissolved into the solution in any number of ways, such as the procedure illustrated in Example 1. In other non-limiting examples, it may be bubbled through the solution, for example, using a vaporizer, or it may be solubilized by agitation or by sonication. In one embodiment, a halogenated volatile compound may be measured in liquid form and directly mixed into a solution. Of course, other suitable methods of dissolving the halogenated volatile compound into solution may also be used. After the halogenated volatile compound has been formulated, it may be administered to a subject in need of pain reduction.

In one aspect, pharmaceutical compositions of the present invention comprise an effective amount of one or more halogenated volatile compound dissolved or dispersed in a pharmaceutically acceptable carrier. The preparation of a pharmaceutical composition that contains at least one halogenated volatile compound will be known to those of skill in the art in light of the present disclosure, as exemplified by Remington, The Science and Practice of Pharmacy ($20^{th}$ Ed., 2000), which is incorporated herein by reference in its entirety. Moreover, for animal (for example, human) administration, it will be understood that preparations should meet sterility, pyrogenicity, and general safety and purity standards as required by FDA Office of Biological Standards.

In one embodiment, the compositions of the present invention further comprise cyclodextrin. Cyclodextrins are a general class of molecules composed of glucose units connected to form a series of oligosaccharide rings (Challa et al., 2005, AAPS PharmSciTech 6:E329-E357). In nature, the enzymatic digestion of starch by cyclodextrin glycosyltransferase (CGTase) produces a mixture of cyclodextrins comprised of 6, 7 and 8 anhydroglucose units in the ring structure (α-, β-, and γ-cyclodextrin, respectively). Commercially, cyclodextrins are also produced from starch, but different, more specific enzymes are used. Cyclodextrins have been employed in formulations to facilitate the delivery of cisapride, chloramphenicol, dexamethasone, dextromethoraphan, diphenhydramine, hydrocortisone, itraconazole, and nitroglycerin (Welliver & McDonough, 2007, Sci World J, 7:364-371). In one embodiment, the cyclodextrin of the invention is hydroxypropyl-Beta-cyclodextrin, sulfobutylether-beta-cyclodextrin, alpha-dextrin or combinations thereof. In another embodiment, cyclodextrin is used as a solubilizing agent.

In one embodiment, a preservative or stabilizer may be included in the composition or solution. For example, the prevention of the action of microorganisms may be brought about by preservatives such as various antibacterial and antifungal agents, including but not limited to parabens (for example, methylparabens, propylparabens), chlorobutanol, phenol, sorbic acid, EDTA, metabisulfite, benzyl alcohol, thimerosal or combinations thereof. Agents that may be included suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). The compositions are preferably sterile and should be fluid in case of injection. Solutions are preferably stable under the conditions of manufacture and storage and must be preserved against the contaminating action of microorganisms, such as bacteria and fungi. Non-limiting examples of stabilizers which may be included include buffers, amino acids such as glycine and lysine, carbohydrates such as dextrose, mannose, galactose, fructose, lactose, sucrose, maltose, sorbitol, and mannitol. Appropriate stabilizers or preservatives may be selected according to the route of administration desired. A particle filter or microbe filter can be used, and may be necessary according to the route of administration desired.

The composition may be sterilized prior to administration. Methods for sterilization are well known in the art and include heating, boiling, pressurizing, filtering, exposure to a sanitizing chemical (for example, chlorination followed by dechlorination, UV radiation exposure or removal of chlorine from solution), aeration, autoclaving, and the like.

Emulsions

As would be understood by one of skill, an emulsion consists of a mixture of two or more immiscible liquids (i.e., contains multiple phases). Emulsions are thus distinct from solutions, which contain one or essentially only one phase. One of the liquids (the dispersed phase) is dispersed in the other (the continuous phase). In one type of emulsion, a continuous liquid phase surrounds droplets of water (for example, a water-in-oil emulsion). In another type of emulsion, oil is dispersed within a continuous water phase (for example, an oil-in-water emulsion). Similarly, emulsification is the process by which emulsions are prepared.

In one embodiment, the compositions of the invention comprise an emulsion, such as a water-in-oil or an oil-in-water emulsion, including, but not limited to a lipid emulsion, such as a soybean oil emulsion. For example, the compositions of the invention comprise a lipid emulsion or an oil-in-water emulsion. Lipid compositions, lipid emulsions, water-in-oil emulsions, and/or oil-in-water emulsions may be useful for the intrathecal, epidural, transdermal, topical, mucosal, buccal, rectal, vaginal, intramuscular, or subcutaneous delivery of the compositions of the invention. Certain emulsions of isoflurane have been prepared previously for intravenous (da Silva Telles et al., 2004, Rev. Bras. Anaestesiol Campianas 54(5):2004) or epidural administration (Chai et al., 2008, Br. J. Anesth. 100:109-115; Chai et al., 2006, Anesth. 105:A743), both for inducing anesthesia.

The emulsion of the invention may further comprise an emulsifier. Emulsions of the invention may also include, but are not limited to, nanoemulsions, which are emulsions with a mean droplet size less than those of emulsions. Nanoemulsions are sometimes referred to as microemulsions and submicroemulsions. Often, the physical appearance of a nanoemulsion is transparent, rather than the often milky appearance of an emulsion, due to the reduced mean droplet size.

In one embodiment, the emulsion of the invention has a lipid component. In another embodiment, the lipid component comprises an amount ranging from about 1% to 99%, from about 5% to about 75%, from about 10% to about 60%, from about 20% to about 50%, or from about 30% to about 40%, w/w of the emulsion. In yet another embodiment, the lipid component of the emulsion is soybean oil, long chain triglyceride, castor oil, corn oil, cottonseed oil, olive oil, peanut oil, peppermint oil, safflower oil, sesame oil, soybean oil, hydrogenated soybean oil, hydrogenated vegetable oil, medium chain triglycerides coconut oil, palm seed oil and derivatives, medium chain (C8/C10) mono- and diglycerides, d-alpha-tocopherol, soy fatty acids, or combinations thereof. In yet another embodiment, the lipid component of the emulsion is soybean oil. Commercially available lipid compositions that may be useful for the production of the volatile anesthetic compositions of the present invention include, but are not limited to, INTRALIPID®, LIPOSYN®, and NUTRILIPID®.

In one embodiment, the emulsion further comprises an emulsifier or emulgent. An emulsifier may also be a surfactant. In one embodiment, the emulsifier ise egg phospholipid, purified egg phospholipids, Polyoxyl 35 castor oil (Cremophor EL), Polyoxyl 40 hydrogenated castor oil (Cremophor RH 40), Polyoxyl 60 hydrogenated castor oil (Cremophor RH 60), Polysorbate 20, Polysorbate 80, d-alpha-tocopheryl polyethylene glycol 1000 succinate, Solutol HS-15, propylene glycol or combinations thereof. Various concentrations of an emulsifier may be used with the present invention. For example, the compositions of the present invention may comprise about 0.1%-99%, 0.1%-60%, 5%-50%, 10%-40%, 5%-25%, 10%-30%, 10%-25%, 25%-50%, 10%-75%, 25%-75%, 10%-65%, 25%-65%, 10%-60%, 25%-60%, 0.1%, 1%, 5%, 10%, 20%, 25%, 30%, 35%, 40%, 45%, 50%, 55%, 60%, 65%, 70%, 75%, 80% or any range derivable therein, of an emulsifier.

In one embodiment, the emulsion of the invention has a perfluorocarbon component. In another embodiment, the perfluorocarbon component comprises an amount ranging from about 0.1% to 99%, from about 5% to about 75%, from about 10% to about 60%, from about 20% to about 50%, or from about 30% to about 40%, w/w of the emulsion. In yet another embodiment, perfluorocarbon is advantageous due to its limited toxicity and ability to scavenge a large amount of gas.

Liposomes and Microdroplets

In one embodiment, the compositions of the invention are encapsulated, micro-encapsulated or nano-encapsulated. In one embodiment, the compositions of the invention comprise a liposome suspension.

A liposome (for example, multilamellar, unilamellar, and/or multivesicular liposomes) is a microscopic, spherical, fluid-filled structure, with walls comprising one or more layers of phospholipids and molecules similar in physical and/or chemical properties to those that make up mammalian cell membranes. By way of non-limiting examples, liposomes may be formed from a variety of natural membrane components, such as cholesterol, stearylamine, or phosphatidylcholine (for example, U.S. Pat. Nos. 5,120,561 and 6,007,838, each of which is incorporated herein by reference in its entirety), or of pure surfactant components like DOPE (dioleoylphosphatidylethanolamine). Liposomes may be formulated to incorporate a wide range of materials as a payload either in the aqueous or in the lipid compartments or in both. Generally, lipophilic active substances dissolve in the bilayer, amphiphilic substances become associated with the phospholipid membrane and hydrophilic substances occur in solution in the enclosed aqueous volume (Artmann et al., 1990, Drug Res. 40 (II) Nr. 12 pp. 1363-1365; incorporated herein by reference in its entirety).

Liposomes useful as drug carriers or for topical use are non-toxic and available in industry (Gehring et al., 1990, Drug Res. 40 (II) Nr. 12, pp. 1368-1371; incorporated herein by reference in its entirety). Liposomes have been used as carriers for lipophilic drugs like the anti-tumor and the anti-viral derivatives of azidothymidine (AZT) (Kamps, et al., 1996, Biochim. Biophys. Acta 1278:183-190). Insulin has also been delivered via liposomes (Muramatsu et al., 1999, Drug Dev. Ind. Pharm. 25:1099-1105). For medical uses as drug carriers, the liposomes may be injected, and when they are modified with lipids, their surfaces become more hydrophilic and hence their ability to persist can be increased. Polyethylene glycol-modified liposomes have been used as carriers for hydrophilic (water-soluble) anti-cancer drugs like doxorubicin. Liposomal derivatives of mitoxantrone and others are especially effective in treating diseases that affect the phagocytes of the immune system because they tend to accumulate in the phagocytes, which recognize them as foreign invaders (Rentsch et al., 1997, Br. J. Cancer 75:986-992). The versatility of liposomes, due to the variable composition, enables liposomes to be used to deliver vaccines, proteins, nucleotides, plasmids, drugs, cosmetics, or the volatile anesthetics of the invention to the body.

Liposome compositions of the invention can comprise any range of liposome and other components, according to the methods and detailed description set forth herein. By way of a non-limiting example, a liposome component of a composition of the invention may include from 0.1% to 99.9% liposome component, or more preferably, from 0.1%-50% liposome component, and even more preferably, from 0.1%-30% liposome component. In one embodiment, the liposome of the invention comprises cholesterol, stearylamine, phosphatidylcholine, dioleoylphosphatidylethanolamine, or combinations thereof.

In one embodiment, the compositions of the invention comprise a microdroplet. A microdroplet of the invention consists of a sphere of organic liquid phase drug that ranges in diameter from about 200 Angstroms to about 10,000 Angstroms that is covered by a monolayer of a suitable lipid. Preferred lipids are phospholipids, which are natural constituents of biological membranes and as such are biologically compatible. Compounds useful for preparing microdroplets include phosphatidylcholine (lecithin), sphingomyelin, phosphatidic acid, phosphatidyl serine, phosphatidyl inositol, diphosphatidyl glycerol and phosphatidyl glycerol.

Microdroplets may be prepared by sonication, including probe or bath sonication, homogenization, microfluidization or by high intensity mechanical agitation. The preferred method of preparing the microdroplets of the invention is by sonication with a probe sonicator. Alternatively, microdroplets may be prepared in a bath sonicator. For small scale preparations a 1.0 cm diameter test tube is suspended, with use of a test-tube clamp, in a bath sonicator filled with water. The components of the microdroplet are first grossly mixed by shaking, Vortex mixing, Polytron or other methods. The suspension is then introduced into the bath sonicator and sonicated for 1-2 hours. If the preparation is to be done on a large scale, it is possible to omit the test tube and introduce the components of the microdroplet directly into a bath sonicator. Microdroplets may also be produced by high intensity mechanical agitation. Useful methods include a Waring blender, a Polytron and high frequency shakers such as a commercial paint shaker. Other materials and methods useful in the preparation of microdroplets are known in the art and are described in U.S. Pat. Nos. 4,622,219, 4,725,442, 5,091,188, Haynes et al. (1989, J Controlled Release 9:1-12) and Haynes et al. (1985, Anesthesiology 63:490-499), all of which references are incorporated herein in their entirety.

Methods

The invention includes a method of treating or preventing pain in a subject in need thereof. The method comprises administering to the subject a therapeutically effective amount of a composition of the invention, whereby the pain in the subject is treated or prevented. The invention further includes a method of dressing a wound in a subject.

In one aspect, the compositions of the invention are administered to the subject by a route other than orally, intravenously, or by inhalation. Preferably, the administration comprises local or regional delivery, such as, for example, transdermal, topical, mucosal, buccal, rectal, vaginal, intramuscular, subcutaneous, intrathecal or epidural delivery, of a composition of the invention to the subject in an amount effective to reduce chronic or acute pain. In one embodiment, the composition of the invention is administered dermally in an amount sufficient to reduce or prevent pain. As used herein, the phrase "pain reduction" is intended to cover pain reduction as a result of anesthesia, analgesia, and/or the inhibition of neural impulses involved in pain perception, e.g., via partial nerve conduction block. In one embodiment, the composition of the invention is delivered to a portion of the subject in an amount and in a manner effective to reduce pain. In another embodiment, the composition of the invention is delivered to a portion of the subject in an amount and in a manner effective to reduce pain without substantially interfering with motor function of the subject. In yet another embodiment, the compositions of the invention reduce the time of wound healing or recovery. In yet another embodiment, the wound is in the skin of the subject.

The delivery of the composition may be continuous, periodic, a one-time event, or the composition may be both periodically administered and continuously administered to the subject on separate occasions. If the administration is intrathecal or epidural, the composition may be free or essentially free of a lipid emulsion. The composition may be delivered intrathecally, epidurally, or in a nerve block procedure, to relieve, for example, chronic pain or acute pain. In one embodiment, the composition is administered locally or topically prior to a procedure such as a venipuncture, an injection (e.g., BOTOX™), a peripheral venous cannulation, incision, hair removal, tattoo application and removal, mammography, or other procedure. In another embodiment, the volatile anesthetic composition is administered via nontopical routes.

Combination Therapies

In one aspect, the compositions of the invention comprise a halogenated volatile compound and at least one anesthetic and/or analgesic. The at least one anesthetic and/or analgesic may comprise a commercially available compound that is known to provide anesthesia to a subject. In one embodiment, the anesthetic and/or analgesic is at least one selected from group consisting of lidocaine, tetracaine, benzocaine, prilocaine, a non-steroidal anti-inflammatory drug (such as but not limited to ibuprofen and diclofenac), another analgesics suitable for topical delivery (such as, but not limited to, acetaminophen and ketamine), a salt thereof and mixtures thereof.

In one embodiment, the at least one anesthetic and/or analgesic is physically separated from the halogenated volatile compound. In another embodiment, the at least one anesthetic and/or analgesic is in physical contact with the halogenated volatile compound. In yet another embodiment, the at least one anesthetic and/or analgesic is incorporated in a medical patch. In yet another embodiment, the halogenated volatile compound is incorporated in a medical patch. In yet another embodiment, the at least one anesthetic and/or analgesic and halogenated volatile compound are incorporated in a medical patch.

In one non-limiting embodiment, once the composition comprising a halogenated volatile compound and at least one anesthetic and/or analgesic is administered to the subject, the halogenated volatile compound provides analgesia within a short period of time from the administration, and the at least one anesthetic and/or analgesic provides analgesia within a longer period of time from the administration. In another non-limiting embodiment, the composition comprising the halogenated volatile compound and the at least one anesthetic and/or analgesic provides substantially continuous pain relief to the subject. In yet another non-limiting embodiment, the halogenated volatile compound and the at least one anesthetic and/or analgesic act synergistically in reducing or preventing pain in the subject.

A synergistic effect between the halogenated volatile compound and at least one anesthetic may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Dosing

The amount of the composition of the invention to be administered, for example, dermally, depends on the particular indication desired. For example, the dose depends on the type of pain intended to be treated. The dose may be different, for instance, if the delivery of the composition is intended to reduce chronic pain as opposed to acute pain. The subject's physical characteristics may also be important in determining the appropriate dosage. Characteristics such as weight, age, and the like may be important factors. For example, the composition may have increased potency with age.

The particular dosage may also be dependent on the dosing regime chosen. For example, the composition may be delivered continuously or periodically. Conversely, the composition may be administered as a single administration as a one-time event.

The concentration of the halogenated volatile compound in solution may vary. For example, a solution may contain a halogenated volatile compound in a w/w ratio of from about 5 to about 95%, from about 10 to about 90%, from about 20 to about 90%, from 50 to about 90%, from about 60 to about 80%, from about 60 to about 75%, from about 20 to about 80%, from about 25 to about 75%, from about 30 to about 70%, from about 40 to about 60%, from about 1 to about 15%, from about 1 to about 10%, from about 1 to about 5%, or any range derivable therein.

The dosing and manner of delivery of the compositions of the invention may be adjusted to achieve pain prevention or reduction without substantially interfering with motor function of the subject, for example, by varying the amount, concentration, frequency of administration, and timing of administration.

The compositions of the invention may also contain one or more additives, such as a surfactant, PVP, a polymer, an antimicrobial agent, a preservative etc. In one embodiment, a composition of the present invention comprises about 0.1-90% of a halogenated volatile compound such as isoflurane, methoxyflurane, or sevoflurane, 0.1-99% of a solvent such as NMP or DMSO, and 0-50% other additive(s) (for example, glycerol, a surfactant, or PVP). In one embodiment, it may be desirable to produce a concentrated formulation which may be subject to a final dilution prior to administration.

Compositions of the invention may be administered regionally or locally by a route other than orally, intravenously or by inhalation. "Regional" or "local" administration allow for the preferential delivery of a composition of the invention to a specific region of the body, such as near a nerve or a nerve bundle. In contrast, systemic/general administration allows for the systemic administration of a volatile anesthetic, for example, via intravenous administration. Regional or local administration typically allows for a lower total body concentration (although elevated local concentrations) of a composition to be administered to a subject for analgesia or diminished pain perception of at least a portion of the subject's body. In one embodiment, the compositions of the invention include from about 100 to about 750,000 ng/mg, from about 100 to about 250,000 ng/mg, from about 100 to about 100,000 ng/mg, from about 100 to about 50,000 ng/mg, from about 100 to about 25,000 ng/mg, or from about 100 to about 10,000 ng/mg of the halogenated volatile compound. The specific concentration of halogenated volatile compound used may vary depending on the desired effect, and in various embodiments the volatile anesthetic composition is titrated for effect: thus the concentration of halogenated volatile compound used or achieved in tissues may vary depending on the specific desired result and/or the particular characteristics of the patient such as sensitivity to the halogenated volatile compound.

The present invention may be used with various nerve block procedures. Nerve block procedures according to the present invention may be performed with or without ultrasound visualization; for example, an ultrasound machine may be used to visualize the region of the body involved in the nerve block procedure, such as, for example, various nerve bundles in the shoulder, neck, lower back, etc. The inventors envision that the present invention may be used in conjunction with a variety of surgical procedures, including, for example, but not limited to, knee replacement, hip replacement, shoulder replacement, and/or birthing-related procedures.

In one embodiment, compositions and methods of the present invention may be used for pain management. Pain management is distinct from general anesthesia in that a lower total body concentration of a halogenated volatile compound may be administered to a subject to increase analgesia or decrease perception of pain, preferably without rendering the subject unconscious or substantially interfering with motor function. In one embodiment, specific concentrations of a halogenated volatile compound used for pain management include from about 100 to about 750,000 ng/mg, from about 100 to about 250,000 ng/mg, from about 100 to about 100,000 ng/mg, from about 100 to about 50,000 ng/mg, from about 100 to about 25,000 ng/mg, or from about 100 to about 10,000 ng/mg of the halogenated volatile compound.

Local topical administration to achieve analgesia prior to or during a medical procedure may be accomplished using techniques known in the art. Examples of such medical procedures include, but are not limited to, surgery, venipuncture, injection, peripheral venous cannulation, incision, suturing, or other procedure.

Other routes of administration contemplated include injection, infusion, continuous infusion, localized perfusion bathing target cells directly, via a catheter, via nanoparticle delivery, topical administration (for example, in a carrier vehicle, a topical control release patch, in a wound dressing, a hydrocolloid, a foam, or a hydrogel), intra-articular, intracranial, and/or intratumoral. An appropriate biological carrier or pharmaceutically acceptable excipient may be used. Compounds administered may, in various embodiments, be racemic, isomerically purified, or isomerically pure.

In one embodiment, the compositions of the invention are not administered intravenously. Intravenous administration typically results in the rapid distribution of the composition throughout the body of a subject. Thus, in certain embodiments, intravenous administration is incompatible for use with regional or local analgesia.

Those skilled in the art recognize, or are to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

It is contemplated that any embodiment discussed in this specification can be implemented with respect to any method or composition of the invention, and vice versa. Furthermore, compositions of the invention can be used to achieve methods of the invention.

The following examples further illustrate aspects of the present invention. However, they are in no way a limitation of the teachings or disclosure of the present invention as set forth herein.

Other objects, features and advantages of the present invention will become apparent from the detailed description herein. It should be understood, however, that the detailed description and the specific examples, while indicating specific embodiments of the invention, are given by way of illustration only, since various changes and modifications within the spirit and scope of the invention will become apparent to those skilled in the art from this detailed description.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Formulation Manufacturing Method

All excipients except for viscosity enhancer(s)/gelling agents (i.e., hydroxypropyl cellulose GF or hydroxypropyl cellulose MF) were measured into a vessel that can be sealed to prevent loss of any volatile compounds present in the formulation (active or excipient). The vessel was made of material compatible for use with isoflurane and the various excipients (e.g., glass). The vessel was sealed at all times except when adding excipients or active. This mixture was then stirred using an appropriate method for the batch size (e.g., magnetic stir bar, mixer) to completely mix all the added excipients.

Isoflurane was then added with a 5% overage to account for any loss during compounding or sample transfer. After addition of the active, the formulation was stirred until uniform.

For those formulations wherein a viscosity enhancer/gelling agent was present, the agent was slowly added and mixed until all agent was completely incorporated. If the formulation viscosity became too high to mix using the stirring method (i.e., magnetic stir bar) an additional mixing using an appropriate method was performed. The formulation was stored overnight to complete solvation. On the next day, one final mixing was performed prior to use or transfer to another container for storage.

Example 2: In Vivo Testing Method Using Pinprick

The analgesic effect of topically applied formulations on the skin was assessed in an in vivo rat model using a pinprick test.

Twenty four hours prior to testing, the dorsal thoracolumbar area of each rat was shaved. On the testing day, formulation was applied to a foil-backed gauze pad (2 cm×2 cm). Pads were applied (gauze side down) to the shaved thoracolumbar region, sealed with occlusive adhesive wrap and maintained for the five or ten minute application period. Following the desired application time, the pad was removed and any remaining drug wiped away.

Analgesia was then assessed at intervals by performing a series of six pinpricks with a von Frey instrument. As a control, an untreated area was also tested in the same manner. Rats normally responded to pinprick with a muscle reflex, vocalization or avoidance. Inhibition of such response was assessed following drug treatment.

Example 3: Evaporation Studies

Figure 3:
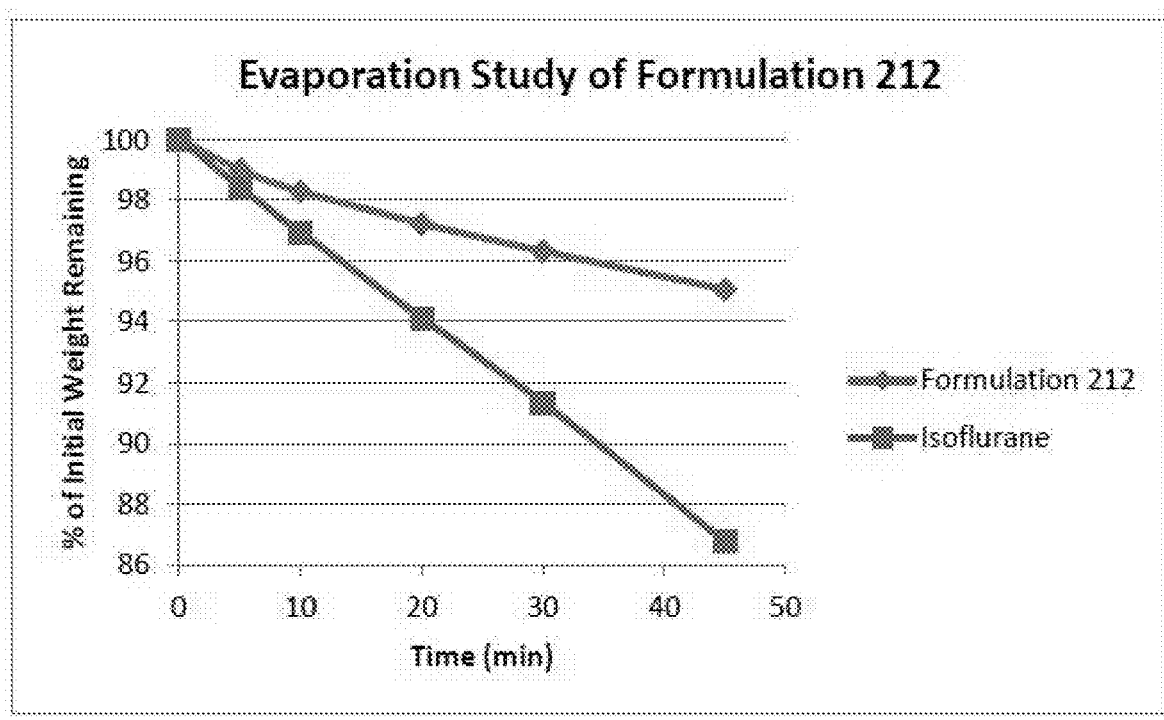
FIG. 3 is a graph illustrating a time-dependent evaporation study of Formulation 212. Control is isoflurane alone.

A time-dependent evaporation study was performed with a composition of the invention (FIG. 3). Isoflurane alone was used as the control in the experiment. As illustrated in FIG. 3, the volatility of the volatile anesthetic in the composition of the invention was reduced as compared to the neat volatile anesthetic. After 45 minutes of experiment, 95.06% of original weight of Formulation 212 remained (i.e., 4.94% of the composition was lost due to evaporation), while only 86.8% of neat isoflurane remained (i.e., 13.2% of isoflurane was lost to evaporation).

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of reducing or ameliorating pain in a subject, the method comprising administering to the subject a therapeutically effective amount of a uniform composition comprising a halogenated volatile compound and hydroxypropyl cellulose (HPC);
wherein the halogenated volatile compound is selected from the group consisting of isoflurane, halothane, enflurane, sevoflurane, desflurane, methoxyflurane, and any mixtures thereof.

2. The method of claim 1, wherein the composition comprises about 5% to about 95% w/w halogenated volatile compound.

3. The method of claim 1, wherein the composition comprises about 50% to about 90% w/w halogenated volatile compound.

4. The method of claim 1,
wherein the composition further comprises at least one selected from the group consisting of an alcohol; a polyol; an organic solvent; an organic carbonate; a fatty acid or a salt thereof; a polyethylene glycol (PEG); a polypropylene glycol (PPG); a copolymer of 2-(2-hydroxypropoxy)propan-1-ol (PPG-12) and 1-methylene bis-4-isocyanatocyclohexane (SMDI); a poloxamer; saccharine; 2-(2-ethoxyethoxy)-ethanol; a monoester of a (methyl vinyl ether-maleic acid) co-polymer; and any combinations thereof;
wherein the polyol is selected from the group consisting of ethylene glycol, propylene glycol, glycerol, and any mixtures thereof,
wherein the organic solvent is selected from the group consisting of dimethylsulfoxide (DMSO), dimethylisosorbide, and any mixtures thereof, and
wherein the organic carbonate is selected from the group consisting of propylene carbonate, ethylene carbonate and any mixtures thereof.

5. The method of claim 4, wherein at least one applies:
the alcohol is selected from the group consisting of methanol, ethanol, n-propanol, isopropanol, n-butanol, sec-butanol, isobutanol, t-butanol, and any mixtures thereof;
the fatty acid or salt thereof is selected from the group consisting of myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, and any combinations thereof;
the PEG is selected from the group consisting of PEG-200, PEG-300, PEG-400, PEG-600, PEG-[950-1,050], PEG-1,000, PEG-[1,300-1,600], PEG-[1,305-1,595], PEG-1,450, PEG-1,500, PEG-2,000, PEG-2,050, PEG-3,000, PEG-[3,000-3,700], PEG-3,350, PEG-4,000, PEG-4,600, PEG-6,000, PEG-8,000, PEG-10,000, PEG-12,000, PEG-20,000, PEG-35,000, and any mixtures thereof;
the monoester of the (methyl vinyl ether-maleic acid) co-polymer is n-butyl, isopropyl, ethyl, or any mixtures thereof;
the poloxamer comprises at least one of poloxamer 188, poloxamer 407, and any mixtures thereof.

6. The method of claim 4, wherein the composition comprises at least one of the following:
about 2% to about 20% w/w alcohol;
about 5% to about 20.25% w/w polyol;
about 5% to about 50% w/w organic solvent;
about 2.5% w/w organic carbonate;
about 1% to about 5% w/w fatty acid or a salt thereof;
about 6% to about 78% w/w PEG;
about 15% to about 20% w/w monoester of a (methyl vinyl ether-maleic acid) co-polymer;
about 5% to about 15% w/w copolymer of PPG-12 and SMDI;
about 2% w/w saccharine;
about 15% to about 20% w/w PPG;
about 1% to about 5% w/w poloxamer.

7. The method of claim 4, wherein the alcohol is ethanol, and wherein the composition comprises a % w/w ethanol concentration selected from the group consisting of: about 8.25%, about 10%, about 10.5%, about 12.5%, about 14.25%, about 15%, and about 20% w/w.

8. The method of claim 4, wherein the composition comprises a % w/w 2-(2-ethoxyethoxy)-ethanol concentration selected from the group consisting of about 5% and about 10% w/w.

9. The method of claim 4, wherein the composition comprises a w/w polyol concentration selected from the group consisting of: about 5%, about 8%, about 14.75%, about 15%, about 15.25% and about 20.25% w/w.

10. The method of claim 4, wherein the composition comprises from about 10% to about 50% w/w organic solvent.

11. The method of claim 1, wherein the composition comprises about 1% to about 5% w/w HPC.

12. The method of claim 1, wherein the composition comprises a w/w HPC concentration selected from the group consisting of: about 1.75%, about 2%, about 2.25%, about 2.5%, and about 5% w/w.

13. The method of claim 4, wherein the composition comprises about 3% w/w fatty acid or a salt thereof.

14. The method of claim 4, wherein the composition comprises a % w/w PEG concentration selected from the group consisting of: about 6%, about 9%, about 10%, about 15%, about 18.25%, about 20%, about 20.5% and about 78%.

15. The method of claim 4, wherein the composition comprises about 20% w/w monoester of a (methyl vinyl ether-maleic acid) co-polymer.

16. The method of claim 4, wherein the composition comprises about 10% w/w copolymer of PPG-12 and SMDI.

17. The method of claim 4, wherein the composition is selected from the group consisting of:
(a) about 28% w/w DMSO, about 10% w/w copolymer of PPG-12 and SMDI, about 2% w/w HPC, and about 60% w/w isoflurane;
(b) about 25% w/w DMSO, about 5% w/w HPC, and about 70% w/w isoflurane;
(c) about 3% w/w oleic acid, about 14.75% w/w propylene glycol, about 1.75% w/w HPC, about 20.5% w/w PEG-400, and about 60% w/w isoflurane;
(d) about 23% w/w DMSO, about 15% w/w PPG-400, about 2% w/w HPC, and about 60% w/w isoflurane;
(e) about 8% w/w propylene glycol, about 2% w/w HPC, about 20% w/w isopropyl alcohol, and about 70% w/w isoflurane;
(f) about 38.25% w/w DMSO, about 1.75 w/w HPC, and about 60% w/w isoflurane;
(g) about 3% w/w oleic acid, about 15% w/w propylene glycol, about 14.25% w/w ethanol, about 1.75% w/w HPC, about 1% w/w poloxamer 407, about 5% w/w poloxamer 188, and about 60% w/w isoflurane;
(h) about 10.5% w/w ethanol, about 20% w/w monoester of a (methyl vinyl ether-maleic acid) co-polymer, about 2.5% w/w propylene carbonate, about 5% w/w 2-(2-ethoxyethoxy)ethanol, about 2% w/w HPC, and about 60% w/w isoflurane;
(i) about 35% w/w DMSO, about 5% w/w HPC, and about 60% w/w isoflurane;
(j) about 3% w/w oleic acid, about 15.25% w/w propylene glycol, about 10% w/w ethanol, about 1.75% w/w HPC, about 10% w/w PEG-400, and about 60% w/w isoflurane;
(k) about 10% w/w copolymer of PPG-12 and SMDI, about 8.25% w/w ethanol, about 20% w/w monoester of a (methyl vinyl ether-maleic acid) co-polymer, about 1.75% w/w HPC, and about 60% w/w isoflurane;
(l) about 10% w/w DMSO, about 5% w/w HPC, and about 85% w/w isoflurane;
(m) about 20% w/w DMSO, about 5% w/w HPC, and about 75% w/w isoflurane;
(n) about 3% w/w oleic acid, about 14.75% w/w propylene glycol, about 2.25% w/w HPC, about 20% w/w PEG-400, and about 60% w/w isoflurane;
(o) about 3% w/w oleic acid, about 15% w/w propylene glycol, about 2% w/w HPC, about 20% w/w PEG-400, and about 60% w/w isoflurane;
(p) about 20% w/w monoester of a (methyl vinyl ether-maleic acid) co-polymer, about 1.75% w/w HPC, about 18.25% w/w PEG-400, and about 60% w/w isoflurane;
(q) about 18% w/w DMSO, about 20% w/w monoester of a (methyl vinyl ether-maleic acid) co-polymer, about 2% w/w HPC, and about 60% w/w isoflurane;
(r) about 5% w/w DMSO, about 5% w/w HPC, and about 90% w/w isoflurane;
(s) about 3% w/w oleic acid, about 10% w/w copolymer of PPG-12 and SMDI, about 15.25% w/w propylene glycol, about 10% w/w ethanol, about 1.75% w/w HPC, and about 60% w/w isoflurane;
(t) about 37.5% w/w DMSO, about 2.5% w/w HPC, and about 60% w/w isoflurane; and
(u) about 3% w/w oleic acid, about 20.25% w/w propylene glycol, about 15% w/w ethanol, about 1.75% w/w HPC, and about 60% w/w isoflurane.

18. The method of claim 1, wherein the composition is incorporated in a medical patch.

19. A method of reducing or ameliorating pain in a subject in need thereof, the method comprising administering to the subject a therapeutically effective amount of a uniform composition comprising a halogenated volatile compound and a monoester of a (methyl vinyl ether-maleic acid) co-polymer;
wherein the halogenated volatile compound is selected from the group consisting of isoflurane, halothane, enflurane, sevoflurane, desflurane, methoxyflurane, and any mixtures thereof.

20. The method of claim 19, wherein the composition comprises about 5% to about 95% w/w halogenated volatile compound.

21. The method of claim 19, wherein the composition comprises about 50% to about 90% w/w halogenated volatile compound.

22. The method of claim 19,
wherein the composition further comprises at least one selected from the group consisting of an alcohol; a polyol; an organic solvent; an organic carbonate; a fatty acid or a salt thereof; a polyethylene glycol (PEG); a polypropylene glycol (PPG); a copolymer of 2-(2-hydroxypropoxy)propan-1-ol (PPG-12) and 1-methylene bis-4-isocyanatocyclohexane (SMDI); a poloxamer; saccharine; 2-(2-ethoxyethoxy)-ethanol; hydroxypropyl cellulose (HPC); and any combinations thereof;
wherein the polyol is selected from the group consisting of ethylene glycol, propylene glycol, glycerol, and any mixtures thereof,
wherein the organic solvent is selected from the group consisting of dimethylsulfoxide (DMSO), dimethylisosorbide, and any mixtures thereof, and
wherein the organic carbonate is selected from the group consisting of propylene carbonate, ethylene carbonate and any mixtures thereof.

23. The method of claim 22, wherein at least one applies:
the alcohol is selected from the group consisting of methanol, ethanol, n-propanol, isopropanol, n-butanol, sec-butanol, isobutanol, t-butanol, and any mixtures thereof;
the fatty acid or salt thereof is selected from the group consisting of myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, and any combinations thereof;
the PEG is selected from the group consisting of PEG-200, PEG-300, PEG-400, PEG-600, PEG-[950-1,050], PEG-1,000, PEG-[1,300-1,600], PEG-[1,305-1,595], PEG-1,450, PEG-1,500, PEG-2,000, PEG-2,050, PEG-3,000, PEG-[3,000-3,700], PEG-3,350, PEG-4,000, PEG-4,600, PEG-6,000, PEG-8,000, PEG-10,000, PEG-12,000, PEG-20,000, PEG-35,000, and any mixtures thereof;
the poloxamer comprises at least one of poloxamer 188, poloxamer 407, and any mixtures thereof.

24. The method of claim 22, wherein the composition comprises at least one of the following:
about 2% to about 20% w/w alcohol;
about 5% to about 20.25% w/w polyol;
about 5% to about 50% w/w organic solvent;
about 2.5% w/w organic carbonate;
about 1% to about 5% w/w fatty acid or a salt thereof;
about 6% to about 78% w/w PEG;
about 5% to about 15% w/w copolymer of PPG-12 and SMDI;
about 2% w/w saccharine;
about 15% to about 20% w/w PPG;
about 1% to about 5% w/w poloxamer;
about 1% to about 5% w/w HPC.

25. The method of claim 22, wherein the alcohol is ethanol, and wherein the composition comprises a % w/w ethanol concentration selected from the group consisting of: about 8.25%, about 10%, about 10.5%, about 12.5%, about 14.25%, about 15%, and about 20% w/w.

26. The method of claim 22, wherein the composition comprises a w/w 2-(2-ethoxyethoxy)-ethanol concentration selected from the group consisting of about 5% and about 10% w/w.

27. The method of claim 22, wherein the composition comprises a % w/w polyol concentration selected from the group consisting of: about 5%, about 8%, about 14.75%, about 15%, about 15.25% and about 20.25% w/w.

28. The method of claim 22, wherein the composition comprises from about 10% to about 50% w/w organic solvent.

29. The method of claim 22, wherein the composition comprises a w/w HPC concentration selected from the group consisting of: about 1.75%, about 2%, about 2.25%, about 2.5%, and about 5% w/w.

30. The method of claim 22, wherein the composition comprises about 3% w/w fatty acid or a salt thereof.

31. The method of claim 22, wherein the composition comprises a w/w PEG concentration selected from the group consisting of: about 6%, about 9%, about 10%, about 15%, about 18.25%, about 20%, about 20.5% and about 78%.

32. The method of claim 19, wherein the monoester of the (methyl vinyl ether-maleic acid) co-polymer is n-butyl, isopropyl, ethyl, or any mixtures thereof.

33. The method of claim 19, wherein the composition comprises about 15% to about 20% w/w monoester of (methyl vinyl ether-maleic acid) co-polymer.

34. The method of claim 19, wherein the composition comprises about 20% w/w monoester of (methyl vinyl ether-maleic acid) co-polymer.

35. The method of claim 22, wherein the composition comprises about 10% w/w copolymer of PPG-12 and SMDI.

36. The method of claim 22, wherein the composition is selected from the group consisting of:
   (a) about 12.5% w/w ethanol, about 20% w/w monoester of a (methyl vinyl ether-maleic acid) co-polymer, about 2.5% w/w propylene carbonate, about 5% w/w 2-(2-ethoxyethoxy)ethanol, and about 60% w/w isoflurane;
   (b) about 10.5% w/w ethanol, about 20% w/w monoester of a (methyl vinyl ether-maleic acid) co-polymer, about 2.5% w/w propylene carbonate, about 5% w/w 2-(2-ethoxyethoxy)ethanol, about 2% w/w HPC, and about 60% w/w isoflurane;
   (c) about 10% w/w copolymer of PPG-12 and SMDI, about 8.25% w/w ethanol, about 20% w/w monoester of a (methyl vinyl ether-maleic acid) co-polymer, about 1.75% w/w HPC, and about 60% w/w isoflurane;
   (d) about 20% w/w monoester of a (methyl vinyl ether-maleic acid) co-polymer, about 1.75% w/w HPC, about 18.25% w/w PEG-400, and about 60% w/w isoflurane;
   (e) about 18% w/w DMSO, about 20% w/w monoester of a (methyl vinyl ether-maleic acid) co-polymer, about 2% w/w HPC, and about 60% w/w isoflurane.

37. The method of claim 19, wherein the composition is incorporated in a medical patch.

\* \* \* \* \*